(12) United States Patent
Sun

(10) Patent No.: US 11,534,438 B2
(45) Date of Patent: Dec. 27, 2022

(54) COMPOSITION CONTAINING PIPERACILLIN, PHARMACEUTICAL FORMULATION THEREOF AND USE THEREOF

(71) Applicant: XIANGBEI WELMAN PHARMACEUTICAL CO., LTD., Hunan (CN)

(72) Inventor: Tianyu Sun, Beijing (CN)

(73) Assignee: XIANGBEI WELMAN PHARMACEUTICAL CO., LTD., Hunan (CN)

( * ) Notice: Subject to any disclaimer, the term of this patent is extended or adjusted under 35 U.S.C. 154(b) by 175 days.

(21) Appl. No.: 16/771,429

(22) PCT Filed: Dec. 25, 2017

(86) PCT No.: PCT/CN2017/118177
§ 371 (c)(1),
(2) Date: Jun. 10, 2020

(87) PCT Pub. No.: WO2019/126910
PCT Pub. Date: Jul. 4, 2019

(65) Prior Publication Data
US 2021/0069183 A1 Mar. 11, 2021

(51) Int. Cl.
| | | |
|---|---|---|
| *A61K 31/496* | (2006.01) | |
| *A61K 31/43* | (2006.01) | |
| *A61P 31/04* | (2006.01) | |
| *A61K 9/00* | (2006.01) | |
| *A61K 9/19* | (2006.01) | |

(52) U.S. Cl.
CPC .......... *A61K 31/496* (2013.01); *A61K 9/0019* (2013.01); *A61K 9/19* (2013.01); *A61K 31/43* (2013.01); *A61P 31/04* (2018.01)

(58) Field of Classification Search
CPC ........ A61K 31/496; A61K 31/43; A61P 31/04
See application file for complete search history.

(56) References Cited

FOREIGN PATENT DOCUMENTS

| CN | 1850046 A | * | 10/2006 |
| CN | 1850046 A | | 10/2006 |

OTHER PUBLICATIONS https://www.fda.gov/inspections-compliance-enforcement-and-criminal-investigations/inspection-guides/lyophilization-parenteral-793, 2014 pp. 1-22. (Year: 2014).*
Translation of CN1850046A, https://worldwide.espacenet.com/patent/search/family/037131558/publication/CN1850046A?q=CN1850046%20A, accessed Mar. 25, 2022, pp. 1-22. (Year: 2022).*
J. Brauers: "Activities of various beta-lactams and beta-lactam beta-lactamase inhibitor combinations against Acinetobacter baumannii and Acinetobacter DNA group 3 strains" European Society of Clinical Microbiology and Infectious Diseases (2004) CMI, 11, 24-30 10.1111/j.1469-0691.2004.01015.x.
Supplementary European search report EP17936693 dated Jun. 23, 2021 (1 Page).
Hung : "In vitro activities of various piperacillin and sulbactam combinations against bacterial pathogens isolated from Intensive Care Units in Taiwan: SMART 2004 programme data", International Journal of Antimicrobial Agents 29 (2007) 145-152.
International Search Report dated Sep. 28, 2018 issued in corresponding PCT/CN2017/118177 application (3 pages).
R. Yan, "Drug Resistance Analysis of Acinetobacter Baumannii", Journal of Guiyang College of Traditional Chinese Medicine, vol. 34, No. 6 (Dec. 31, 2012).

* cited by examiner

*Primary Examiner* — Craig D Ricci
*Assistant Examiner* — Janet L Coppins
(74) *Attorney, Agent, or Firm* — Millen, White, Zelano & Branigan, PC; Ryan Pool

(57) ABSTRACT

The present disclosure provides a piperacillin-containing composition, which further containing a certain proportion of ampicillin and sulbactam. The present disclosure further provides a pharmaceutical formulation thereof and the use thereof. The composition and pharmaceutical formulation of the present disclosure can inhibit the drug-resistant *Acinetobacter baumannii*, and particularly have therapeutic effects on the infection caused by *Acinetobacter baumannii* which is resistant to carbapenem or cefoperazone-sulbactam.

12 Claims, No Drawings

COMPOSITION CONTAINING PIPERACILLIN, PHARMACEUTICAL FORMULATION THEREOF AND USE THEREOF

TECHNICAL FIELD

The present disclosure relates to a piperacillin-containing composition and the use thereof.

BACKGROUND

*Acinetobacter baumannii* has emerged as an important pathogen causing infection in various systems such as respiratory tract, blood, abdominal cavity, central nervous system, urinary tract, skin and soft tissue. According to a report from China Antimicrobial Surveillance Network (CHINET) in 2016, *A. baumannii* was the most common pathogen recovered from respiratory samples, suggesting it may play a very important role in respiratory tract diseases. Pulmonary infection caused by *A. baumannii* has become an important cause of death, especially for critical patients of long-term hospitalization. In addition, *A. baumannii* accounted for 10.8% of all clinical bacteria isolates, just behind *Escherichia coli* and *Klebsiella pneumoniae*.

For a long time, penem and carbapenem antibiotics have efficient therapeutic effect on *A. baumannii* infection. However, with widespread use, *A. baumannii* is developing resistance to multiple and extensive drugs. Most of *A. baumannii* have been insensitive to penem. Though other drugs such as polymyxin and cefoperazone-sulbactam can be used for clinical treatment, the use of polymyxin is limited due to its strong nephrotoxicity, and the cefoperazone-sulbactam resistance of *A. baumannii* has developed increasingly prominent.

According to a report from CHINET in 2010, the resistance rate of *A. baumannii* to cefoperazone-sulbactam was 30%, while such rate had increased to 43% as shown by a report from CHINET in 2016. Therefore, there is an urgent clinical demand for more safe and effective drugs for the treatment of drug-resistant *A. baumannii* infection.

SUMMARY

One objective of the present disclosure is to overcome the drug resistance, especially cefoperazone-sulbactam resistance of *Acinetobacter baumannii*.

The development of drug resistance in bacteria involves complex mechanism which includes producing drug-inactivating enzymes, altering drug targets, changing bacterial membrane permeability, overexpressing efflux pumps, and the like.

Piperacillin is a commonly used penicillin antibiotic in clinical practice. However, it is reported that the resistance rate of *A. baumannii* to piperacillin has reached over 70%. The inventor surprisingly found that a composition comprising piperacillin and further components had excellent antibacterial activity on *A. baumannii*, thereby achieving the purpose of the present disclosure.

The present disclosure provides a piperacillin-containing composition, which further comprises ampicillin and sulbactam, wherein the composition comprises piperacillin, ampicillin and sulbactam in a weight ratio of 200-400:0.02-6:100.

Preferably, the composition of the present disclosure may comprise piperacillin, ampicillin and sulbactam in a weight ratio of 200-400:0.02-3:100, further preferably in a weight ratio of 200:0.02-3:100, 300:0.02-3:100, or 400:0.02-3:100. According to another preferred embodiment, the composition of the present disclosure may comprise piperacillin, ampicillin and sulbactam in a weight ratio of 200-400:0.04-6:100, further preferably in a weight ratio of 200:0.04-6:100, 300:0.04-6:100, or 400:0.04-6:100.

Preferably, the composition of the present disclosure may consist of piperacillin, ampicillin and sulbactam.

The present disclosure also provides a pharmaceutical formulation, which comprises the composition according to the present disclosure.

Preferably, the pharmaceutical formulation may be an injection. Further preferably, the injection may be a powder for injection, or be a solution for injection which is prepared by dissolving the powder with a solvent. The powder for injection may be a sterile powder injection or lyophilized powder for injection. The solvent may be a conventional solvent suitable for clinical practice, such as aqueous solutions of glucose or sodium chloride.

The composition or pharmaceutical formulation of the present disclosure may be prepared by conventional processes in the art.

The present disclosure further provides a method for treating a bacterial infection disease, which comprises administering the composition or pharmaceutical formulation according to the present disclosure. Alternatively, the present disclosure further provides use of the composition or pharmaceutical formulation in the manufacture of a medicament for treating a bacterial infection disease.

Preferably, the bacteria may be drug-resistant *A. baumannii*.

Further preferably, the drug-resistant *A. baumannii* is resistant to cefoperazone-sulbactam.

It should be noted that the terms "piperacillin", "ampicillin" or "sulbactam" as used in the present disclosure are general terms. That is, piperacillin, ampicillin or sulbactam may refer to various forms thereof, such as free acid, salt, polymorph, hydrate or solvate thereof. For example, some common ones may include piperacillin acid ((2S,5R,6R)-3,3-dimethyl-6-[(R)-2-(4-ethyl-2,3-dioxo-1-piperazinecarboxamido-2-phenylacetamido]-7-oxo-4-thia-1-azabicyclo[3.2.0]heptane-2-carboxylic acid), piperacillin sodium (sodium (2S,5R,6R)-3,3-dimethyl-6-[(R)-2-(4-ethyl-2,3-dioxo-1-piperazinecarboxamido)-2-phenylacetamido]-7-oxo-4-thia-1-azabicyclo[3.2.0]heptane-2-carboxylate), ampicillin acid ((2S,5R,6R)-3,3-dimethyl-6-[(R)-2-amino-2-phenyl acetylamino]-7-oxo-4-thia-1-azabicyclo[3.2.0]heptane-2-carboxylic acid), ampicillin sodium (sodium (2S,5R,6R)-3,3-dimethyl-6-[(R)-2-amino-2-phenyl acetylamino]-7-oxo-4-thia-1-azabicyclo[3.2.0]heptane-2-carboxylate), sulbactam acid ((2S,5R)-3,3-dimethyl-7-oxo-4-thia-1-azabicyclo[3.2.0]heptane-2-carboxylic acid-4,4-dioxide), sulbactam sodium (sodium (2S,5R)-3-dimethyl-7-oxo-4-thia-1-azabicyclo[3.2.0]heptane-2-carboxylate-4,4-dioxide), and the like.

The pharmaceutical formulation according to the present disclosure refers to a pharmaceutical drug product which is produced according to the requirements for certain dosage forms and can be directly used by individuals. The composition according to the present disclosure may comprise an amount of water or impurities. The pharmaceutical formulation according to the present disclosure may comprise an amount of excipients.

The piperacillin-containing composition according to the present disclosure further comprises an amount of sulbactam and ampicillin to improve the drug resistance of *A. baumannii*. Although a sulbactam-containing formulation has been used in the prior art for the treatment of *A. baumannii* infection, it generally believed that it is sulbactam per se responsible for the antibacterial effect. In contrast, the present disclosure found for the first time that a small amount of ampicillin incorporated in the composition can significantly improve the antibacterial effect on drug-resistant *A. baumannii*. Its mechanism may be that ampicillin increases the permeability of cell membrane by attacking the drug-resistant bacteria, which leads to the increase in the probability and concentrations of other drugs in bacterial cells.

The composition and formulation according to the present disclosure can be used for clinical treatment of infection diseases caused by drug-resistant *A. baumannii*, and have excellent anti-bacterial effect even when *A. baumannii* is resistant to cefoperazone-sulbactam and other drugs. Therefore, the present disclosure has remarkable technical effects and clinic al advantages.

DETAILED DESCRIPTION

Hereinafter the present disclosure will be illustrated in details with reference to examples, but they are not intended to limit the technical solution and technical effect of the present disclosure.

Example 1: Preparation of a Piperacillin-Containing Composition

Piperacillin sodium (1000 g calculated by piperacillin acid), ampicillin sodium (0.1 g calculated by ampicillin acid) and sulbactam sodium (500 g calculated by sulbactam acid) were taken and mixed well in a mono-cone ribbon mixer, to obtain a composition. One part of the composition was subpackaged under sterile condition to obtain a powder for injection (sterile powder for injection). The other part of the composition was dissolved by 100× (ml/g) of 0.9% aqueous sodium chloride solution, and then subpackaged to obtain solutions for injection.

Example 2: Preparation of a Piperacillin-Containing Composition 1000 g of piperacillin acid, 0.3 g of ampicillin acid and 500 g of sulbactam acid were dissolved in an aqueous solution containing 343 g sodium bicarbonate, and then lyophilized and subpackaged to obtain powder for injection (lyophilized powder for injection) containing the composition.

Examples 3-6: Preparation of a Piperacillin-Containing Composition

The preparation processes of examples 3-6 were similar to that of example 1. The amounts of piperacillin and sulbactam were the same as those of example 1. While, the amounts of ampicillin gradually increased in examples 3-6, and were 1 g, 3 g, 10 g and 15 g, respectively.

Comparative Examples 1-2

The preparation processes of comparative examples 1-2 were similar to that of example 1. The amounts of piperacillin and sulbactam were the same as those of example 1. While, in comparative examples 1-2, the amounts of ampicillin were 60 g and 200 g, respectively.

Comparative Example 3

The preparation process of comparative example 3 was similar to that of example 1. The amounts of piperacillin and sulbactam were the same as those of example 1. While no ampicillin was included in comparative example 3.

Examples 7-8: Preparation of a Piperacillin-Containing Composition

The preparation processes of examples 7-8 were similar to that of example 1. In both examples 7 and 8, the amounts of piperacillin and sulbactam were 1500 g and 500 g, respectively. While, the amounts of ampicillin were 5 g and 15 g, respectively, in examples 7 and 8.

Example 9: Preparation of a Piperacillin-Containing Composition

Piperacillin sodium (1000 g calculated by piperacillin acid), 0.1 g of ampicillin acid and sulbactam sodium (250 g calculated by sulbactam acid) were mixed well in a multi-direction movement mixer, to obtain a composition. A part of the resulted composition was subpackaged under a sterile condition to obtain powder for injection.

Examples 10-14: Preparation of a Piperacillin-Containing Composition

The preparation processes of examples 10-14 were similar to that of example 9. The amounts of piperacillin and sulbactam were the same as that of example 9. While, the amounts of ampicillin gradually increased in examples 10-14, and were 0.2 g, 0.7 g, 3 g, 5 g and 15 g, respectively.

Comparative Examples 4-5

The preparation processes of comparative examples 4-5 were similar to that of example 9. The amounts of piperacillin and sulbactam were the same as that of example 9. While the amounts of ampicillin were 80 g and 300 g, respectively, in comparative examples 4 and 5.

Experimental Example 1: Study of Protective Effect of Different Compositions on *Acinetobacter Baumannii* Infection in Experimental Animals Experimental materials: Tested samples were the compositions obtained in examples 1-14 and comparative examples 1-5, as well as meropenem, sulbactam and cefoperazone-sulbactam. Tested animals were ICR mice. Tested bacterial strains were ATCC19606 (a standard strain of *A. baumannii*), CBP-R (a carbapenem-resistant strain of *A. baumannii*), and CPZ/S-R (a cefoperazone-sulbactam-resistant strain of *A. baumannii*). Among them, the standard strain was obtained from ATCC, and the other strains were clinically isolated.

Determining the dose ranges of the tested samples: The tested strains were diluted with 5% high active dry yeast to obtain bacterial dilutions of different concentrations ($10^{-1}$, $10^{-2}$, $10^{-3}$, and $10^{-4}$), and then intraperitoneally injected into the tested animals in 0.5 ml/mice. The number of dead mice after infection was recorded. The minimum bacterial dose, which kills 100% members of the mice, was recorded as 1 MLD. The mice were infected with 1 MLD of bacteria which was formulated with 5% high active dry yeast Immediately and 6 hours after the infection, a preliminary experiment was carried out with high, median and low dosages of the tested samples, and the survival numbers of the mice after infection were recorded. Based on the results of the preliminary experiment, the administration dosages of the tested samples were designed for the animal protection experiment. The appropriate administration dosage was one that resulted in more than 70% of the infected animals survived in the group administered with the highest dosage, and more than 70% of the infected animals died in the group administered with the lowest dosage.

Animal protection experiment: After fasting with water only for 18 h, the mice (half male and female, 25-30 g body weight) were randomly divided into: (1) ATCC19606 group, (2) CBP-R group, and (3) CPZ/S-R group. Each group was treated with five concentrations of the samples, and included 10 animals. In addition, 10 animals were incorporated as a control group. Each mouse was intraperitoneally injected with 0.5 ml of 1 MLD bacterial solution to establish an infection model. At 0 h and 6 h after infection, the mice were subcutaneously injected with different concentrations of the tested samples, 0.2 ml/mice, and the mice of the control group were injected with the same volume of sterilized water. The animals were observed continuously for 7 days, and the death of animals in each group was recorded. The 50% effective dose ($ED_{50}$) of each tested sample was calculated by the Bliss method. Smaller $ED_{50}$ means that the tested sample has better anti-bacterial effect in vivo, and better protective effect on the experimental animals.

Test results: S, A, B, C, D represented the different grades of $ED_{50}$. S: $ED_{50} \leq 20$ mg/kg; A: 20 mg/kg<$ED_{50} \leq 50$ mg/kg; B: 50 mg/kg<$ED_{50} \leq 100$ mg/kg; C: 100 mg/kg<$ED_{50} \leq 200$ mg/kg; D: $ED_{50}$>200 mg/kg. Table 1 shows the main results of this experiment.

TABLE 1

$ED_{50}$ of different compositions for animals infected with *A. baumannii*

| | Strains | | |
|---|---|---|---|
| Tested samples | ATCC19606 a standard strain of *A. baumannii* | CBP-R a carbapenem-resistant *A. baumannii* | CPZ/S-R a cefoperazone-sulbactam resistant *A. baumannii* |
| Meropenem | S | D | C |
| Sulbactam | S | C | D |
| Cefoperazone-sulbactam | A | C | D |
| Example 1 | A | B | B |
| Example 2 | A | A | B |
| Example 3 | A | B | B |
| Example 4 | A | B | B |
| Example 5 | A | B | B |
| Example 6 | A | B | B |
| Comparative Example 1 | A | C | C |
| Comparative Example 2 | A | C | D |
| Comparative Example 3 | A | C | C |
| Example 7 | A | B | B |
| Example 8 | A | B | B |
| Example 9 | A | A | B |
| Example 10 | A | B | B |
| Example 11 | A | A | B |
| Example 12 | A | B | B |
| Example 13 | A | B | B |
| Example 14 | A | B | B |
| Comparative Example 4 | A | C | D |
| Comparative Example 5 | A | D | D |

In the above-mentioned experiments, each tested samples showed efficient inhibitory effect on the standard strain of *A. baumannii* without drug resistance, in which single meropenem or sulbactam was more advantageous in pharmaceutical efficacy.

Regarding drug-resistant strains of *A. baumannii*, single meropenem or sulbactam had significantly decreased inhibitory effect, and cefoperazone-sulbactam also failed to provide satisfactory effect. In contrast, the piperacillin-containing composition of the present disclosure had significantly improved anti-bacterial effect, and showed strong synergistic effect. The amount of ampicillin in the composition affects the anti-bacterial effect thereof. The composition having a small amount of ampicillin had better anti-bacterial effect on the drug-resistant *A. baumannii*.

The present disclosure has been described in details with general description, specific examples and experiments. On this basis, those skilled in the art can make reasonable modifications or improvements to the present disclosure. These modifications or improvements without departing from the principle and scope of the present disclosure further belong to the scope of the present disclosure.

INDUSTRIAL APPLICABILITY

The present disclosure provides a piperacillin-containing composition. The composition of the present disclosure comprises piperacillin and further comprises a certain proportion of ampicillin and sulbactam, wherein the weight ratio of piperacillin, ampicillin and sulbactam is 200-400: 0.02-6:100. The present disclosure further provides a pharmaceutical formulation thereof and the use thereof. The composition and pharmaceutical formulation of the present disclosure can significantly inhibit drug-resistant *A. baumannii*, particularly have therapeutic effects on the infection caused by *A. baumannii*, which is resistant to carbapenem or cefoperazone-sulbactam. The composition and pharmaceutical formulation of the present disclosure has significant clinical advantages, and good economic value and application prospect.

The invention claimed is:

1. A piperacillin-containing composition, comprising ampicillin and sulbactam, wherein the composition comprises piperacillin, ampicillin and sulbactam in a weight ratio of 200-400:0.02-6:100.

2. The composition according to claim 1, wherein the composition comprises piperacillin, ampicillin and sulbactam in a weight ratio of 200-400:0.02-3:100, or in a weight ratio of 200-400:0.04-6:100.

3. The composition according to claim 1, the composition consists of piperacillin, ampicillin and sulbactam.

4. A pharmaceutical formulation comprising the composition according claim 1.

5. The pharmaceutical formulation according to claim 4, wherein the pharmaceutical formulation is an injection.

6. The pharmaceutical formulation according to claim 5, wherein the injection is a powder for injection or a solution for injection.

7. The pharmaceutical formulation according to claim 6, wherein the powder for injection is a sterile powder for injection or lyophilized powder for injection.

8. A method for treating a bacterial infection disease, comprising administering the composition according to wherein the bacteria is drug-resistant *Acinetobacter baumannii* claim 1.

9. The method according to claim 8, wherein the drug-resistant *Acinetobacter baumannii* is resistant to cefoperazone-sulbactam.

10. The method according to claim 8, wherein the composition is formulated to a pharmaceutical formulation.

11. The method according to claim 10, wherein the pharmaceutical formulation is an injection.

12. The method according to claim 11, wherein the injection is a powder for injection or a solution for injection.

\* \* \* \* \*